(12) United States Patent
Müller et al.

(10) Patent No.: US 7,211,701 B2
(45) Date of Patent: May 1, 2007

(54) PREPARATION OF TRIMETHYLOLPROPANE

(75) Inventors: Dirk Müller, Bergisch Gladbach (DE); Paul Wagner, Düsseldorf (DE); Brian Schwegler, Visp (CH); Ulrich Notheis, Dormagen (DE); Ralph Armbrust, Dormagen (DE); Hans-Detlef Heinz, Leverkusen (DE); Alexander Wagner, Krefeld (DE)

(73) Assignee: Lanxess Deutschland GmbH, Leverkusen (DE)

( * ) Notice: Subject to any disclaimer, the term of this patent is extended or adjusted under 35 U.S.C. 154(b) by 729 days.

(21) Appl. No.: 10/322,962

(22) Filed: Dec. 18, 2002

(65) Prior Publication Data

US 2003/0139631 A1    Jul. 24, 2003

(30) Foreign Application Priority Data

Dec. 27, 2001    (DE) ................. 101 64 264

(51) Int. Cl.
*C07C 31/22*    (2006.01)
*C07C 29/38*    (2006.01)

(52) U.S. Cl. .............. 568/853; 568/854; 568/861; 568/868

(58) Field of Classification Search ................ 568/853, 568/854, 861, 868
See application file for complete search history.

(56) References Cited

U.S. PATENT DOCUMENTS

| 3,097,245 | A | 7/1963 | Russell et al. .............. 260/635 |
| 3,185,274 | A | 5/1965 | Robeson .................... 260/635 |
| 4,514,578 | A | 4/1985 | Immel et al. ............... 568/853 |
| 2002/0010376 | A1 | 1/2002 | Iwamoto et al. ........... 568/854 |
| 2002/0189926 | A1 | 12/2002 | Dembach et al. ............. 203/14 |

FOREIGN PATENT DOCUMENTS

| DE | 1 154 080 | 9/1963 |
| DE | 45 078 | 1/1966 |
| DE | 287 251 | 2/1991 |
| GB | 1 290 036 | 9/1972 |

OTHER PUBLICATIONS

Chemical Enginneering Research and Design, vol. 70 (A2), 1992, pp. 118-132 (abstract only).*

* cited by examiner

*Primary Examiner*—Elvis O. Price
(74) *Attorney, Agent, or Firm*—Michael A. Miller

(57) ABSTRACT

The present invention relates to a process for preparing trimethylolpropane having a low APHA color number.

22 Claims, 2 Drawing Sheets

PREPARATION OF TRIMETHYLOLPROPANE

BACKGROUND OF THE INVENTION

1. Field of the Invention

The present invention relates to a process for preparing trimethylolpropane having a low APHA (American Public Health Association) colour number.

2. Brief Description of the Prior Art

Trimethylolpropane, referred to hereinbelow as TMP, is a trihydric alcohol of great industrial significance which finds use, for example, in the field of coating resin, powder coating, foam and polyester production.

Customarily, TMP is prepared from n-butyraldehyde and formaldehyde. Base-catalysed aldol reactions initially generate 2,2-dimethylolbutyraldehyde in the 1st reaction step from n-butyraldehyde and two equivalents of formaldehyde. 2,2-Dimethylolbutyraldehyde may then be converted in the 2nd reaction step, for example, by reaction with further formaldehyde and base in a Cannizzaro reaction to TMP-containing reaction mixtures in which the formate of the base used also occurs as a further reaction product.

The reaction steps 1 and 2 may either be carried out separately or in one working step. The bases used both for the base-catalysed reaction step 1 and also for the reaction step 2 which is stoichiometric in relation to the base quantity may optionally each independently be, for example, alkali metal or alkaline earth metal hydroxides or carbonates, or tertiary amines.

When, for example, a tertiary amine is used for the separate $2^{nd}$ reaction step or the reaction steps 1 and 2 carried out in a single working step, this is known as the organic Cannizzaro process. When inorganic bases, for example alkali metal or alkaline earth metal hydroxides or carbonates, are used, this is accordingly known as an inorganic Cannizzaro process. The different physical and chemical properties of the ammonium formates or inorganic formates occurring as the further reaction products require very different work-up methods for the TMP-containing reaction mixtures.

The inorganic Cannizzaro process has the advantage that the TMP occurs in good purity and when, for example, calcium hydroxide is used as the base, the by-product is calcium formate which in turn may be used, for example, as an additive for animal nutrition, in the building materials industry, as an assistant in the leather industry, as an assistant in producing high-gloss papers, for treating scrubbing water and in smoke desulphurization.

The TMP-containing reaction mixtures obtainable by the Cannizzaro process generally have very strong coloration which is caused by impurities. This coloration, which may customarily be evaluated by a colour number according to APHA (American Public Health Association) or Hazen, interferes in some uses, which is why the work-up customarily consists of cleaning operations, for example acid treatments, extractions and/or multistage distillations. Such multistage distillations generally require expensive, space-consuming and column arrangements which are costly and inconvenient in terms of apparatus and are accordingly quite unattractive in economic terms.

Various techniques are known for the work-up of TMP-containing reaction mixtures from inorganic Cannizzaro processes. For example, DD-P-45 078 describes a process for work-up in which TMP-containing reaction mixtures obtained from inorganic Cannizzaro processes are admixed with secondary cycloaliphatic alcohols which form azeotropes with water. Then water is azeotropically distilled off together with this alcohol, and the precipitated alkali metal or alkaline earth metal formates are removed by filtration. After distilling off the excess alcohol, the crude TMP obtained is distilled for further purification.

DD Patent 287 251 discloses a process for removing high boilers from TMP. Examples of high boilers include subsequent reaction products of TMP, in particular formals, which have a higher boiling point than TMP and accordingly accumulate in the distillation residue when crude TMP is vacuum-distilled. In the process described, the addition of from 0.02 to 0.05 kg of acid/kg at least partially converts many of the high boilers back to TMP, which is intended to lead to a yield increase.

GB 1 290 036 also describes a process for decomposing high boilers in TMP-containing reaction mixtures which have been obtained by the inorganic Cannizzaro process. This involves adding cationic exchange resins and heating to from 50° C. to 140° C. to convert any formals present, which have a similar boiling point to TMP and tend to decompose at the boiling point of TMP, to products having other boiling points which can be easily distilled off.

U.S. Pat. No. 3,097,245 describes a process for preparing TMP having an APHA colour number of from 50 to 200. This colour number is achieved by limiting the reaction time to less than 7 hours, acidifying the reaction mixture to a pH of less than 7 and limiting the concentrations of the starting compounds to from 5 to 20% by weight. The reaction is also followed by treatment of the solution obtained with cationic exchange resins and strongly basic quaternary ammonium anion exchangers.

Common to all the processes mentioned is that chemical treatment methods have to be carried out which worsen both the eco-balance and the economic preparability of the product or entail considerable apparatus, and accordingly financial, costs and inconvenience to generate products having an acceptable colour number.

There is accordingly a need to provide an efficient process which makes it possible to obtain pure TMP in high yield and having a very low APHA colour number, i.e. of 20 or less, from the TMP-containing reaction mixtures prepared by the inorganic Cannizzaro process.

SUMMARY OF THE INVENTION

We have now found a process for preparing TMP having a very low APHA colour number, which is characterized by
a) n-butyraldehyde and/or 2,2-dimethylolbutyraldehyde are reacted with formaldehyde in the presence of an inorganic base to give TMP-containing reaction mixtures,
b) water and inorganic salts are at least partially removed from the TMP-containing reaction mixture obtained in a) to recover crude TMP and
c) the crude TMP obtained from b) is separated, optionally after at least partial removal of high boilers and non-boilers, by distillation into one or more low boiler fractions, one or more predominantly TMP-containing medium boiler fractions and one or more high boiler and/or non-boiler fractions.

DETAILED DESCRIPTION OF THE INVENTION

Figure 1:
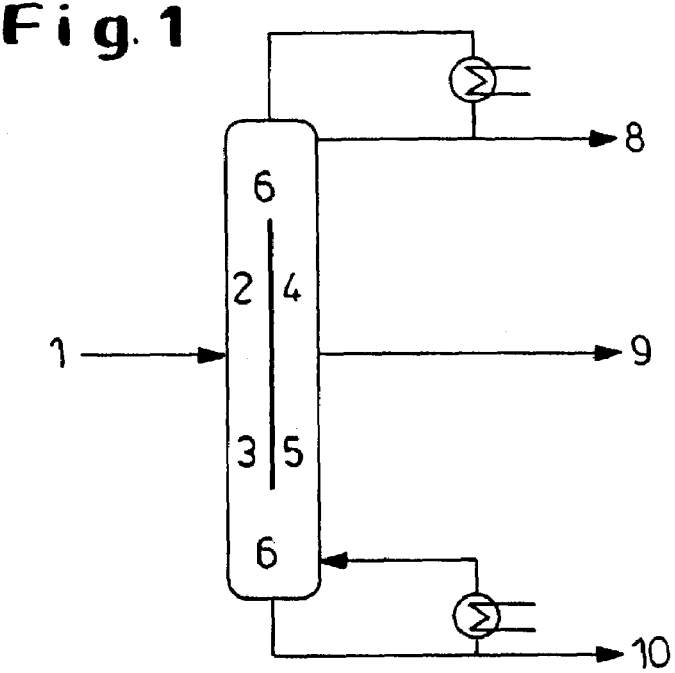
FIG. 1 shows the simplified illustration of the product stream of separation in a dividing wall column.

It is pointed out that the scope of the invention also encompasses any desired combinations of the areas of preference cited hereinbelow.

Step a) of the process according to the invention may be carried out, for example, according to or in a manner similar to the process described by DE-A 11 54 080, U.S. Pat. No. 3,183,274 or WO 01/51438.

Examples of useful inorganic bases include alkali metal or alkaline earth metal hydroxides and/or carbonates. Preference is given to sodium hydroxide, potassium hydroxide, calcium hydroxide, barium hydroxide, sodium carbonate and calcium carbonate or mixtures thereof. Particular preference is given to sodium hydroxide and calcium hydroxide or mixtures thereof, and very particular preference is given to calcium hydroxide.

For example and with preference, formaldehyde may be used in the form of an aqueous solution having a formaldehyde content of from about 1 to 55% by weight, more preferably having a formaldehyde content of from 20 to 40% by weight.

Preference is further given to using formaldehyde which comprises less than 10 mol %, more preferably from 0 to 6 mol % and most preferably from 0 to 4 mol %, of methanol, based on formaldehyde.

In a preferred embodiment, n-butyraldehyde is reacted with formaldehyde in the presence of an inorganic base to give TMP-containing reaction mixtures. The molar ratio of formaldehyde to n-butyraldehyde may be, for example, from 2:1 to 10:1, preferably from 3:1 to 4:1 and more preferably from 3.1:1 to 3.4:1. The use of molar amounts of formaldehyde greater than 10:1 is possible but uneconomical.

The molar ratio of base to n-butyraldehyde may be, for example, from 1.0 to 1.5, preferably from 1.01 to 1.4 and more preferably from 1.02 to 1.3. The use of greater molar amounts of base may, in particular at high reaction temperatures, lead to yield losses through side reactions and is accordingly uneconomical. The valency of the base used has to be taken into account.

The reaction may be carried out, for example, at atmospheric pressure, pressures of from 0.5 bar to atmospheric pressure or pressures of from atmospheric pressure to 10 bar, and preference is given to reaction at atmospheric pressure. It is possible to carry out the reaction at higher pressures, but economically not sensible.

The temperature in the reaction may be, for example, from 0° C. to 100° C., and preference is given to temperatures of from 10° C. to 90° C., and particular preference to temperatures of from 20 to 70° C. Higher temperatures and longer reaction times may lead to a high proportion of undesired side reactions and to more strongly coloured products.

The reaction time may be, for example, from 0.1 to 24 hours, and preference is given to from 0.2 to 4 hours. In individual cases, preferred reaction times may be easily determined by those skilled in the art in a customary manner, for example by following the course of the reaction using analytical methods.

Step a) may provide a TMP-containing reaction mixture. This TMP-containing reaction mixture customarily comprises water and inorganic formates, with or without excess formaldehyde and an excess base, and also products which may stem, for example, from elimination reactions, decomposition reactions and subsequent reactions. Without claiming completeness, these may be, for example:

Linear and branched alcohols, for example 2-ethyl-1,3-propanediol and 2-{[2,2-bis(hydroxylmethyl)butoxy]methyl}-2-ethyl-1,3-propanediol (di-TMP); formals, for example 2-ethyl-2-[(methoxymethoxy)methyl]-1,3-propanediol or 2-({[2,2-bis(hydroxymethyl)butoxy]methoxy}methyl)-2-ethyl-1,3-propanediol (bis-formal); esters such as TMP monoformate and TMP monobutyrate and ethers such as 2-ethyl-2-(methoxymethyl)-1,3-propanediol.

Step b) of the process according to the invention removes water and inorganic salts from the TMP-containing reaction mixture. The water and the inorganic salts may be removed, for example, by extracting the TMP-containing reaction mixture once or more than once with a water-immiscible or only slightly water-miscible solvent. This extraction may be carried out, for example, according to or similar to WO 99/20586 or U.S. Pat. No. 5,603,835.

Examples of useful solvents for the extraction include ethers, aldehydes, ketones, alcohols and esters. Examples of useful ethers are methyl tert-butyl ether, di-n-propyl ether and diglyme, an example of a suitable aldehyde is butyraldehyde, examples of suitable ketones are methyl isobutyl ketone and methyl ethyl ketone, examples of suitable alcohols are 2-ethylhexanol and n-octanol, and examples of suitable esters include those having from 2 to 9 carbon atoms, for example methyl acetate or ethyl acetate. Mixtures of such solvents may also be used.

The solvent used may then be removed in a manner known per se, for example by distillation.

Alternatively, and preferably for the process according to the invention, water is initially removed by means of distillation and the solids which predominantly comprise inorganic salts are then removed.

Inorganic salts are substantially inorganic formates and any unconverted inorganic base.

The distillation may be carried out by methods known per se, and preference is given to the use of one or more evaporator(s), particular preference to the use of multistage evaporation apparatus in which the individual stages are operated at different pressures and accordingly also different temperatures in order to utilize the vapours of individual or multiple stages to heat further stages and thus to distinctly reduce the energy demands compared to one-stage evaporation apparatus.

The pressures in the distillation steps may be, for example, in the range from 20 mbar to 1 bar. Depending on the water content of the mixture, temperatures, for example, in the range from 50 to 120° C. may be obtained at these pressures.

In a preferred embodiment, distillation is continued until the water content of the distillation residue is less than 10% by weight, preferably less than 5% by weight and more preferably less than 2% by weight.

Any solids which are precipitated out may be removed, for example, by filtration, centrifugation or sedimentation and decantation, and preference is given to centrifugation and also to sedimentation and decantation.

The steps of distillation and subsequent removal of any solids which have precipitated may optionally be repeated.

When inorganic calcium bases, for example calcium hydroxide and/or carbonate are used, the solid which precipitates comprises calcium formate which may be put to the above-mentioned uses, optionally after purifying operations.

In the manner described, step b) provides from the TMP-containing reaction mixture obtainable according to step a) crude TMP which has been at least partially freed of water and inorganic formates and has a content of over 75% by weight, preferably over 80% by weight, of TMP.

The crude TMP may be used directly in step c).

Alternatively, the crude TMP provided by step b) may initially be at least partially freed of high boilers and non-boilers.

For the purposes of the invention, high boilers are those organic compounds which have a boiling point higher than that of TMP. For example, but not exclusively, these are compounds such as 2-ethyl-1,3-propanediol, di-TMP and bisformal.

For the purposes of the invention, non-boilers are those compounds which can only be distilled off after irreversible chemical change or not at all. For example, but not exclusively, these include inorganic salts and oligomeric and polymeric compounds having a molar mass of about 300 g/mol and more, or more than three basic units derived from TMP or dimethylbutyraldehyde.

The at least partial removal of high boilers and non-boilers may be effected, for example, by distillation, preferably by distillation using evaporators, for example a thin film evaporator.

The distillation residue which comprises the high boilers and any inorganic salts present may be, for example, disposed of, thermally converted for generating heating steam or utilized to recover compounds, for example di-TMP.

When the process step following step b) is carried out, prepurified crude TMP is obtained which preferably has a content of over 80% by weight, preferably of over 90% by weight, and more preferably of over 94% by weight, of TMP.

The prepurified crude TMP generally has colour numbers of over 100 according to APHA.

The prepurified crude TMP or the crude TMP provided by step b) is separated in step c) by distillation into one or more low boiler fractions, one or more predominantly TMP-containing medium boiler fractions and one or more high boiler fractions. Preference is given to separating the prepurified crude TMP or the crude TMP provided by step b) each into one low boiler fraction, one predominantly TMP-containing medium boiler fraction and one high boiler fraction.

For the purposes of the invention, low boilers are those compounds which have a boiling point lower than that of TMP. For example, but not exclusively, these include residues of water, formaldehyde, 2-ethyl-1,3-propanediol or 2-ethylacrolein.

For the purposes of the invention, predominantly TMP-containing medium boiler fractions are those fractions which have a content of over 90% by weight, preferably over 98% by weight and more preferably over 99% by weight, of TMP, and a colour number according to APHA of 50 or less, preferably 20 or less, more preferably 15 or less and most preferably 10 or less.

The distillation according to the invention of the crude TMP or the prepurified crude TMP may be batchwise or continuous, and preference is given to continuous distillation.

In a particularly preferred embodiment of the process according to the invention, distillation is preferably effected using distillation columns in which one or more low boiler fractions and one or more predominantly TMP-containing medium boiler fractions can be simultaneously withdrawn. Preference is given to those distillation columns which are suitable for side withdrawal of liquid and/or gaseous media, for example sidestream columns, dividing wall columns or thermally coupled distillation columns, and greater preference is given to the use of dividing wall columns in the process according to the invention.

Useful dividing wall columns and thermally coupled columns are cited, for example, in EP-A 122 367, EP-A 0 126 288 and EP-A 0 133 510. Compared to the arrangement of conventional distillation columns, dividing wall columns and thermally coupled columns in particular provide enormous advantages relating both to the energy requirements and to the capital expenditure costs.

Customarily, the low boiler fractions which may comprise colouring components are withdrawn via the top of the column of the distillation apparatus and the predominantly TMP-containing medium boiler fractions are withdrawn via sidestream takeoffs. The remaining distillation residue is customarily a strongly coloured high boiler fraction which may further comprise non-boilers.

Figure 2:
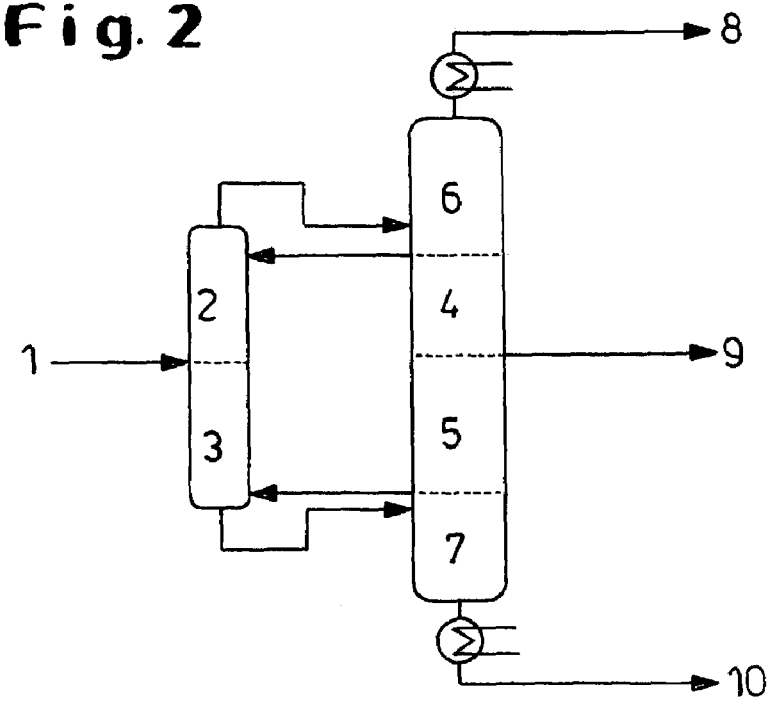
FIGS. 2–4 show illustration of the thermally coupled distillation columns.
Figure 3:
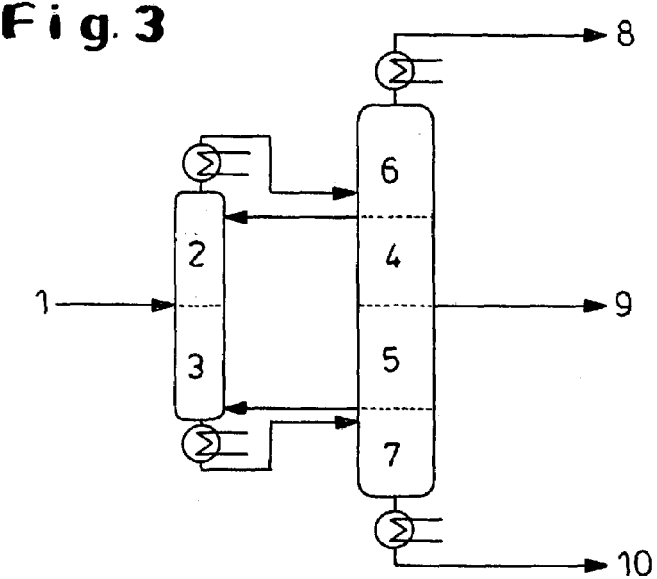
Figure 4:
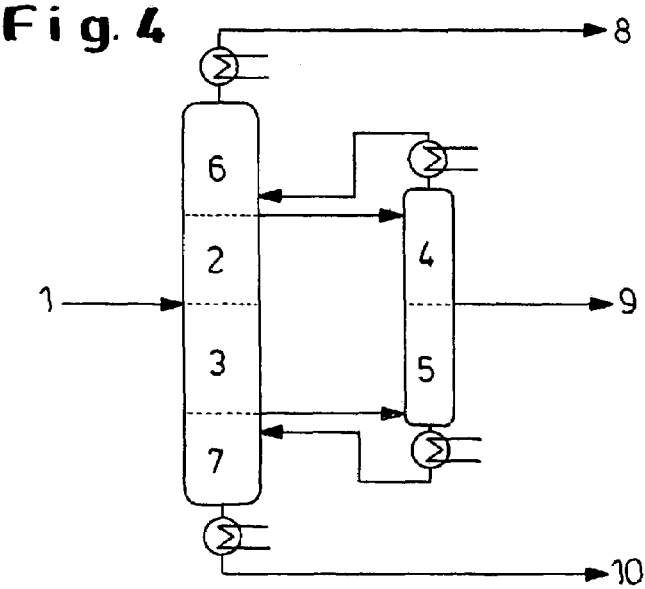

The drawings 1 to 4 (FIG. 1, FIG. 2, FIG. 3, FIG. 4) are used hereinbelow to illustrate by way of example the distillative removal of the crude TMP obtained from b) or of the prepurified crude TMP without limiting the subject-matter of the invention thereto.

Drawing 1 (FIG. 1) shows the simplified illustration of the product stream of separation in a dividing wall column. The numbering chosen applies similarly to the thermally coupled distillation columns illustrated in drawings 2, 3 and 4.

The crude TMP or the prepurified crude TMP [1] is fed to the column via a feed. The column has a feed section [2], [3], a withdrawal section [4], [5], an upper column section (top column section) [6] and a lower column region in which the distillation residue (liquid phase) is customarily found [7].

The low boiler fraction 8 is withdrawn via the top column section [6], the predominantly TMP-containing medium boiler fraction [9] via the withdrawal section [4], [5] and the high boiler fraction [10], which may either be disposed of or thermally converted, for example for generating heating steam, via the lower column region [7].

The continuous removal of the high boiler fraction [10] which may also contain non-boilers has the advantage in particular that the accumulation of high-boiling and/or non-boiling and/or strongly coloured components, which may result from side reactions when crude TMP or prepurified crude TMP are thermally stressed, is avoided.

The dividing wall columns and thermally coupled columns usable according to the invention may, for example and with preference, be configured as packed columns with random packings or ordered packings or as tray columns.

Typical trays, random packings and ordered packings are described, for example, in Henry Kister, Distillation Design, McGrawHill, 1992. High performance packings, for example the packing MellapakPlus® from Sulzer Chemtech, Winterthur/Switzerland, may also be used.

When thermally coupled columns are used, it is advantageous to configure them in such a manner that the connecting streams between the individual distillation columns are exclusively liquid.

When dividing wall columns or thermally coupled columns which are configured as tray columns are used, the number of trays may be, for example, from 4 to 150, preferably from 8 to 70, more preferably from 10 to 45. Preference is given to arranging the trays of dividing wall columns which are configured as tray columns in such a manner that the dividing wall is at an angle of from about 80 to 90° to the corresponding upflow and downflow pipes of the trays.

When dividing wall columns or thermally coupled columns which are configured as packed columns are used, the number of theoretical plates may be, for example, from 5 to 100, preferably from 8 to 50, more preferably from 10 to 35.

It is also possible to provide the column both with trays and with packing elements. For example, packings may be used in the rectifying section and trays in the stripping section.

Dividing wall columns in particular from which liquid or gaseous samples may be withdrawn continuously or batchwise at the upper and lower ends of the dividing wall may also be used for the process according to the invention. Such dividing wall columns, like the above-cited column types, are sufficiently well known to those skilled in the art.

The distillation according to the invention of the crude TMP or of the prepurified crude TMP may be carried out, for example, at a temperature of from 150 to 260° C., preferably from 180 to 250° C. and more preferably from 180 to 235° C. and, for example, at pressures of from 0.5 to 500 mbar, preferably from 2 to 100 mbar, more preferably from 2 to 50 mbar and most preferably from 5 to 30 mbar.

The temperature quoted relates to the liquid phase temperature measured in the lower column region, and the pressure quoted to the values measurable in the top column region.

In order to minimize possible reactions which result from thermal stress on the crude TMP or on the prepurified crude TMP and may form undesired colouring components and accordingly worsen the product quality, preference is given to average residence times in the column of, for example, from 2 minutes to 12 hours, more preferably from 5 minutes to 2 hours.

The predominantly TMP-containing medium boiler fractions obtained according to the invention may be subjected to a renewed purifying operation, for example a renewed distillation, although this is unnecessary.

The TMP prepared according to the invention is suitable in particular for producing coating resins, powder coatings, foams or polyesters.

The process according to the invention has the advantage that TMP having purities of over 99% and colour numbers of less than 10 according to APHA may be obtained from TMP-containing reaction mixtures obtainable by the inorganic Cannizzaro process with low apparatus requirements in a highly efficient manner. Owing to the low energy demands for the distillation according to the invention, the process further provides an ecological and economical advance.

The invention is further illustrated but is not intended to be limited by the following examples in which all parts and percentages are by weight unless otherwise specified.

EXAMPLES

Example 1

In a thermostatized 1 1 jacketed stirred tank equipped with a mechanical stirrer, 400 g of water and 420 g of a 30% aqueous formaldehyde solution are initially charged at 25° C. 54 g of calcium hydroxide are then added and 97 g of butyraldehyde are metered in within one hour. Within this time, the temperature is raised to 45° C. Stirring is continued for 45 minutes, then the mixture is cooled to 25° C. and the reaction mixture is adjusted to pH 6 using 85% formic acid (% by weight). 971 g of a TMP-containing reaction mixture having a TMP content of 15.1% by weight are obtained.

Three batches obtained by the above procedure are combined, concentrated on a rotary evaporator under reduced pressure and filtered through a suction filter. 287 g of damp residue remain on the suction filter which are again slurried with 153 g of water and then filtered with suction. Filtrate and washing liquid are combined and again concentrated on the rotary evaporator under reduced pressure. Weight: 521 g of crude TMP having a TMP content of 80.5% by weight.

Example 2

1.032 g of a TMP reaction solution having a TMP content of 80.5% prepared according to Example 1 are metered from a preheated dropping funnel at a metering rate of 700 g per hour into a thin film evaporator. The thin film evaporator is operated at 215° C. and 8 mbar. Downstream of the thin films, two cooling traps cooled by dry ice are attached.

873 g of prepurified crude TMP having a TMP content of 94.9% (APHA colour number 148) are obtained as the top product and 93 g of highly viscous dark brown bottom products. 37 g of low boilers are isolated from the cooling traps.

Example 3

Prepurified crude TMP for Example 2 was [lacuna] in a distillation apparatus comprising a 1000 mm-high distillation section for concentrating low boilers (rectifying section), a 1500 mm-high middle distillation section arranged below the rectifying section and divided by a dividing wall, and also a 1000 mm-high distillation section for concentrating high boilers and non-boilers (stripping section) arranged below the middle distillation section. The distillation apparatus was further provided at the upper end of the column with a condenser and at the lower end of the column with an evaporator. Furthermore, the apparatus was equipped with a heating mantle to avoid heat losses by monitoring the temperatures both within the column and in the heating mantle and controlling the heating mantle in such a manner that the same temperature profile over the column height is obtained in the column and in the heating mantle.

The distillative separation was effected at a reflux ratio at the top of the column of 48. The feed mass flow was 2.8 kg/h. The top pressure of the apparatus was 75 mbar. At this pressure, a top temperature of 152° C. and a bottom temperature of 216° C. were obtained. By this procedure, TMP having a content of 99.5% by weight and an APHA colour number of 13 was obtained.

Example 4

The crude TMP for Example 2 was distillatively separated in the distillation apparatus described in Example 3 at a top pressure of 15 mbar. At this pressure, a top temperature of 125° C. and a bottom temperature of 184° C. were obtained. As in the first example, the reflux ratio at the top of the column was 48. The feed mass flow was 1.5 kg/h. By this procedure, TMP having a content of 99.1% by weight and also an APHA color number of 8 was obtained.

Example 5 (Comparative Example)

Prepurified crude TMP for Example 2 was separated in two stages in the distillation apparatus from Example 3 by operating the column without the sidestream takeoff. In the first step, low boilers were withdrawn at the top of the column and the product TMP was withdrawn together with high boilers and non-boilers as the bottom product. The distillation was carried out in a similar manner to the distillation in Example 3 at a top pressure of 75 mbar. The top product of the first step was then fed back into the column in order to distil the product TMP overhead and withdraw high boilers and non-boilers as the bottom stream. By this procedure, TMP having a content of 99.3% by weight and an APHA color number of only 22 was obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing trimethylolpropane having a low APHA colour number, comprising:
    a) reacting n-butyraldehyde and/or 2,2-dimethylolbutyraldehyde with formaldehyde in the presence of an inorganic base to give trimethylolpropane-containing reaction mixtures,
    b) removing water and inorganic salts at least partially from the trimethylolpropane-containing reaction mixture obtained in a) to recover crude trimethylolpropane and
    c) separating the crude trimethylolpropane obtained from b) by distillation into one or more low boiler fractions, one or more predominantly trimethylolpropane-containing medium boiler fractions and one or more high boiler fractions whereby, during the distillation, one or more low boiler fractions and one or more predominantly trimethylolpropane-containing medium boiler fractions are simultaneously withdrawn.

2. Process according to claim 1, wherein n-butyraldehyde is reacted in step a) with formaldehyde in the presence of an inorganic base to give trimethyloipropane-containing reaction mixtures.

3. Process according to claim 1, wherein the inorganic base used in step a) is an alkali metal, alkaline earth metal hydroxide or carbonate, or a mixture thereof.

4. Process according to claim 1, wherein the inorganic base used in step a) is sodium hydroxide, calcium hydroxide or a mixture thereof.

5. Process according to claim 1, wherein the inorganic base used in step a) is calcium hydroxide.

6. Process according to claim 1, wherein formaldehyde is used in step a) in the form of an aqueous solution having a formaldehyde content of from 1 to 55% by weight.

7. Process according to claim 1, wherein formaldehyde used in step a) comprises less than 10 mol % of methanol.

8. Process according to claim 1, wherein the molar ratio of formaldehyde to n-butyraldehyde in step a) is from 2:1 to 10:1.

9. Process according to claim 1, wherein the molar ratio of base to n-butyraldehyde in step a) is from 1.0 to 1.4.

10. Process according to claim 1, wherein the pressure in the reaction in step a) is from 0.5 to 10 bar.

11. Process according to claim 1, wherein the reaction temperature in step a) is from 0 to 100° C.

12. Process according to claim 1, where in step b), water is initially removed by means of distillation and the solids are then removed.

13. Process according to claim 12, where distillation is continued in step b) until the water content of the distillation residue is less than 10% by weight.

14. Process according to claim 12, wherein the solids are removed by filtration, centrifugation, or sedimentation and decantation.

15. Process according to claim 12, wherein the removal of water by distillation and the removal of solids are repeated once or more than once.

16. Process according to claim 1, wherein the crude TMP obtained according to step b) is at least partially freed of high boilers and non-boilers before it is fed to step a).

17. Process according to claim 1, wherein the distillation in step c) is operated continuously.

18. Process according to claim 1, wherein, during the distillation, one or more high boiler fractions, optioally comprising non-boilers are simultaneously withdrawn.

19. Process according to claim 1, wherein sidestream columns, dividing wall columns or thermally coupled distillation columns are used for the distillation in step a).

20. Process according to claim 1, wherein dividing wall columns or thermally coupled distillation columns which are configured as tray columns are used for the distillation in step a).

21. Process according to claim 1, wherein dividing wall columns or thermally coupled distillation columns which are equipped in the rectifying section with packings and in the stripping section with trays are used for the distillation in step c).

22. Process according to claim 1, wherein the distillation in step c) is carried out at a temperature of from 170 to 260° C. and a pressure of from 0.5 to 500 mbar.

* * * * *